(12) United States Patent
Katori et al.

(10) Patent No.: US 10,573,158 B2
(45) Date of Patent: Feb. 25, 2020

(54) RADIO EQUIPMENT

(71) Applicant: YOKOGAWA ELECTRIC CORPORATION, Musashino-shi, Tokyo (JP)

(72) Inventors: Kenji Katori, Musashino (JP); Keiichi Sasaki, Musashino (JP); Daisuke Kaneko, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/161,657

(22) Filed: Oct. 16, 2018

(65) Prior Publication Data

US 2019/0147725 A1 May 16, 2019

(30) Foreign Application Priority Data

Nov. 16, 2017 (JP) ................................. 2017-221188

(51) Int. Cl.
| | |
|---|---|
| G08B 21/16 | (2006.01) |
| H01Q 1/24 | (2006.01) |
| H04B 5/00 | (2006.01) |
| G01N 33/00 | (2006.01) |

(52) U.S. Cl.
CPC ......... *G08B 21/16* (2013.01); *G01N 33/0022* (2013.01); *H01Q 1/241* (2013.01); *H04B 5/0043* (2013.01)

(58) Field of Classification Search
CPC .... G08B 21/16; G01N 33/0022; H01Q 1/241; H04B 5/0043; H04W 12/06; H04L 29/06
See application file for complete search history.

(56) References Cited

U.S. PATENT DOCUMENTS

| 5,521,610 A * | 5/1996 | Rodal | .................... | H01Q 9/285 |
| | | | | 343/797 |
| 10,224,615 B2 * | 3/2019 | Wu | .......................... | H01Q 9/42 |
| 2010/0141549 A1 * | 6/2010 | Sato | .................... | H01Q 1/1207 |
| | | | | 343/872 |

(Continued)

FOREIGN PATENT DOCUMENTS

| EP | 2517473 B1 | 4/2013 |
| EP | 3 048 740 A1 | 7/2016 |

(Continued)

OTHER PUBLICATIONS

Extended Search Report dated Mar. 28, 2019, issued in counterpart EP Application No. 18201646.9 (14 pages).

*Primary Examiner* — An T Nguyen
(74) *Attorney, Agent, or Firm* — Westerman, Hattori, Daniels & Adrian, LLP

(57) ABSTRACT

Radio equipment includes a substrate on which a first antenna for near field communication is provided, a base portion on which the substrate is erected, and a cover portion configured to be attached to the base portion so as to cover the substrate. The cover portion includes an opposing portion configured to oppose the first antenna and a non-opposing portion disposed closer to the base portion than the opposing portion in a direction in which the substrate is erected. A distance from an outer surface of the cover portion to the substrate at the opposing portion is shorter than a distance from the outer surface of the cover portion to the substrate at the non-opposing portion.

10 Claims, 10 Drawing Sheets

(56) References Cited

U.S. PATENT DOCUMENTS

| | | | | |
|---|---|---|---|---|
| 2014/0125549 A1* | 5/2014 | Kaneko | ............... | H01Q 1/3275 |
| | | | | 343/872 |
| 2014/0361671 A1* | 12/2014 | Degner | ................... | G06F 1/20 |
| | | | | 312/223.2 |
| 2015/0188226 A1* | 7/2015 | Ng | ......................... | H01Q 5/00 |
| | | | | 343/862 |
| 2015/0229021 A1* | 8/2015 | Yukizaki | ............. | H01Q 1/3275 |
| | | | | 343/702 |
| 2016/0112219 A1 | 4/2016 | Lee et al. | | |
| 2019/0145801 A1* | 5/2019 | Sasaki | ................. | G01D 11/245 |
| | | | | 73/649 |
| 2019/0147725 A1* | 5/2019 | Katori | .................. | G08B 21/16 |
| | | | | 340/632 |

FOREIGN PATENT DOCUMENTS

| | | | |
|---|---|---|---|
| WO | 2013/064963 A1 | | 5/2013 |
| WO | WO-2014033994 A1 | * | 3/2014 |

\* cited by examiner

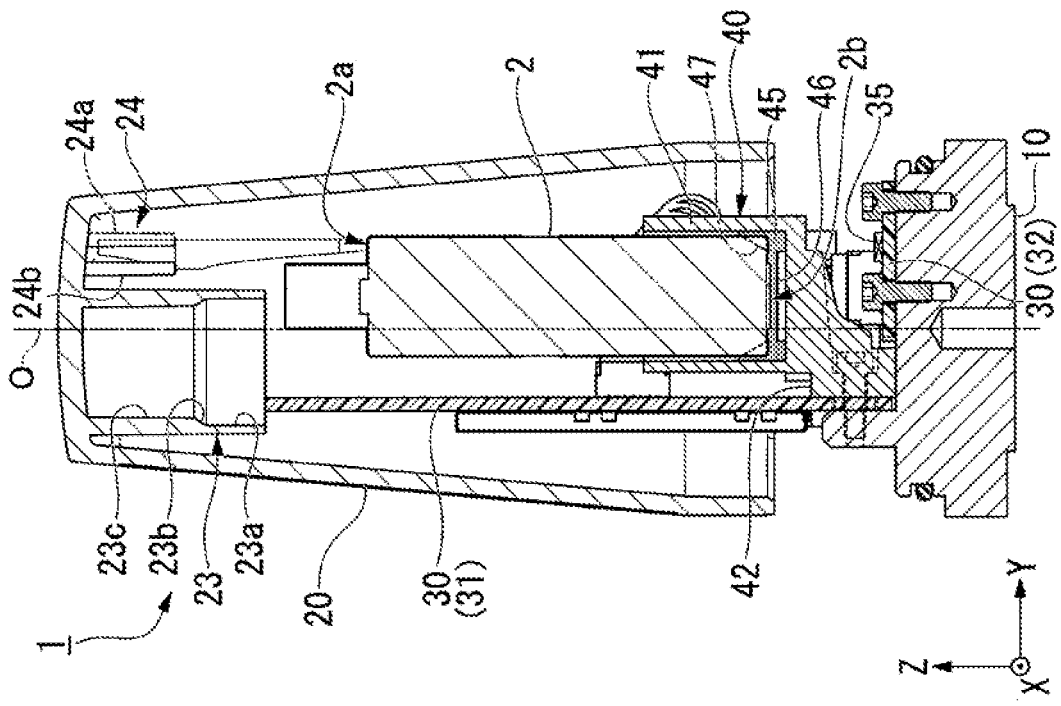
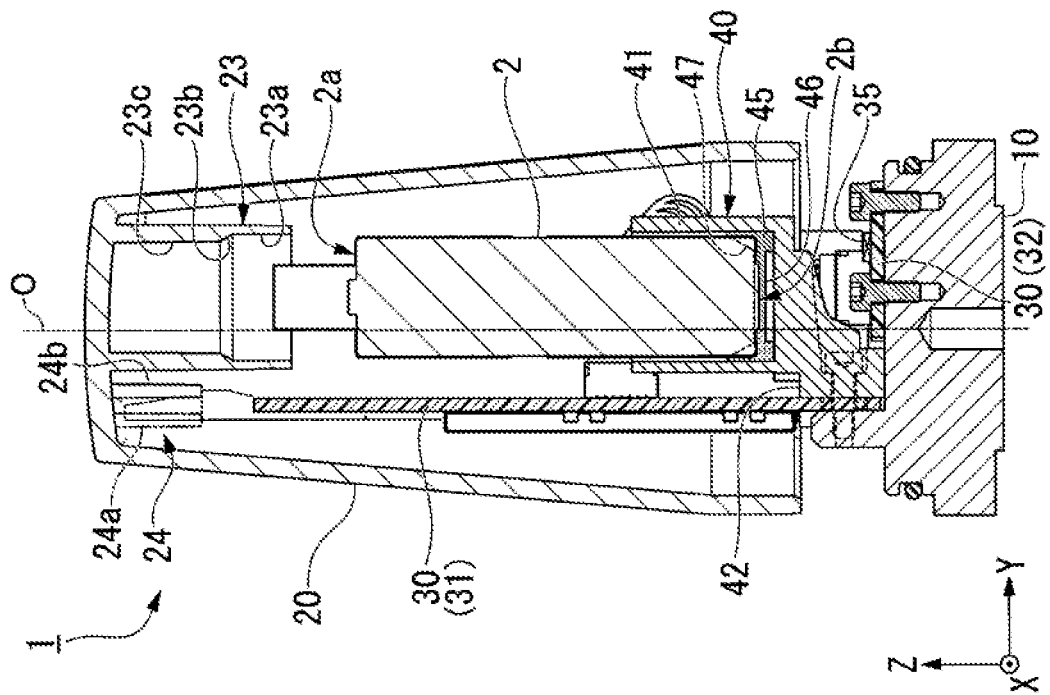

RADIO EQUIPMENT

CROSS-REFERENCE TO RELATED APPLICATION

This application is based upon and claims the benefit of priority from Japanese Patent Application No. 2017-221188 filed on Nov. 16, 2017, the entire disclosure of which is incorporated herein by reference.

TECHNICAL FIELD

This disclosure relates to radio equipment.

BACKGROUND

Patent Literature 1 (PTL 1) below discloses radio equipment configured to monitor the conditions of mechanical equipment within a combustible gas or explosive gas environment. This radio equipment is a radio sensor connected to a radio network where the radio sensor can transmit a detected physical parameter. The radio equipment includes a vibration sensor, a processor, a radio transmitter, a battery and a base portion where these constituent elements are mounted, as well as a cover portion attached to the base portion, configured to cover the equipment mounted on the base portion. The battery is fastened to a substrate supported on the base portion with a clamp. The processor and a radio communication device or the like are mounted on the substrate.

CITATION LIST

Patent Literature

PTL 1: EP2517473B1

SUMMARY

The radio equipment described above can transmit the sensor data by way of the radio network. However, to transmit the sensor data, provisioning needs to be executed from external setting equipment by connecting a cable to a radio communication device in advance. The provisioning is a process of performing necessary settings to allow the radio equipment to join the radio network. In recent years, it has been considered to apply the short-range communication using the near field communication (NFC) to the provisioning to meet the demand for simple provisioning which does not involve the connection of the cable to the radio equipment or the removal of the cover portion.

However, with the radio equipment described above, in general, the base portion on which the substrate is erected is threaded, so that the cover portion is screwed down on to the base portion. In this case, the cover portion has a cylindrical shape. An outer surface of the cylindrical cover portion constitutes a curved surface, while a mounting surface of the substrate on which the NFC antenna is provided constitutes a flat surface. Thus, a space (a distance) is inevitably generated between both the surfaces, whereby the sensitivity of the near field communication is deteriorated. Additionally, with the cylindrical cover portion, the position of the NFC antenna cannot be determined when seen from the outside.

An object of the disclosure is to provide radio equipment that improves the sensitivity of the near field communication.

According to some embodiments of the disclosure, there is provided radio equipment including a substrate on which a first antenna for near field communication is provided, a base portion on which the substrate is erected, and a cover portion configured to be attached to the base portion so as to cover the substrate, wherein the cover portion includes an opposing portion configured to oppose the first antenna and a non-opposing portion disposed closer to the base portion than the opposing portion in a direction in which the substrate is erected, and wherein a distance from an outer surface of the cover portion to the substrate at the opposing portion is shorter than a distance from the outer surface of the cover portion to the substrate at the non-opposing portion.

According to this configuration, the distance from the outer surface of the cover portion to the substrate becomes shorter at the opposing portion of the cover portion which opposes the first antenna for near field communication than at the non-opposing portion of the cover portion which is disposed closer to the base portion than the opposing portion. Thus, the sensitivity of the near field communication becomes better than a case where a cylindrical cover portion is adopted on which the distance to the substrate varies little.

According to one embodiment, an external shape of the cover portion at the opposing portion is smaller than an external shape of the cover portion at the non-opposing portion.

According to this configuration, the external shape of the cover portion becomes smaller at the opposing portion of the cover portion which opposes the first antenna for near field communication than at the non-opposing portion of the cover portion which is disposed closer to the base portion than the opposing portion. Thus, the sensitivity of the near field communication becomes better than a case where a cylindrical cover portion is adopted on which the distance to the substrate varies little.

According to one embodiment, the outer surface of the cover portion forming the opposing portion is formed into a flat plane.

According to this configuration, the opposing portion is formed into a planar shape, whereby the space (the distance) to the substrate can be made smaller than the cylindrical cover portion. Thus, the sensitivity of the near field communication is improved.

According to one embodiment, a mark is formed on the opposing portion, the mark indicating a position where the first antenna is disposed.

According to this configuration, the position where the first antenna is disposed can be determined from the outside of the cover portion. Thus, an information terminal device can easily be moved towards the first antenna.

According to one embodiment, the cover portion includes a substrate holding portion configured to dispose the first antenna to oppose the mark.

According to this configuration, the substrate is held on the cover portion inside the cover portion, whereby the first antenna can be positioned behind the mark. Thus, not only the position where the first antenna is disposed can be determined, but also the sensitivity of the near field communication is improved.

According to one embodiment, the cover portion includes a substrate holding portion configured to dispose the first antenna to oppose the opposing portion.

According to this configuration, the substrate is held on the cover portion inside the cover portion, whereby the first antenna can be positioned behind the opposing portion. Thus, the sensitivity of the near field communication is improved.

According to one embodiment, the base portion has a circular disc shape and includes a screwing mechanism configured to screw the cover portion to an outer circumferential surface of the base portion.

When the substrate holding portion is provided on the cover portion as described above, the cover portion cannot be attached to the base portion through screwing as done in the conventional technique; however, the cover portion can be attached to the base portion by screwing the cover portion to the outer circumferential surface of the base portion.

According to one embodiment, the radio equipment includes a rotation restricting mechanism configured to restrict a relative rotation occurring between the base portion and the cover portion about a screw due to the screwing mechanism.

According to this configuration, when adopting the screwing mechanism as described above, not only loosening between the cover portion and the base portion can be prevented but also a deviation in the opposing positional relationship between the opposing portion and the first antenna can be suppressed by adopting the rotation restricting mechanism.

According to one embodiment, the rotation restricting mechanism guides the base portion and the cover portion for attachment to or detachment from each other in a direction in which the substrate is erected.

According to this configuration, the attachment of the cover portion to the base portion can be facilitated.

According to one embodiment, the cover portion includes a battery holding portion configured to hold a battery which is electrically connected with the substrate, and the substrate holding portion and the battery holding portion have different shapes.

According to this configuration, when the battery is accommodated inside the cover portion, and the battery holding portion is provided on the cover portion, the substrate holding portion and the battery holding portion have the different shapes; therefore, the cover portion can be prevented from being attached in a reverse orientation, whereby the first antenna can be disposed to oppose the opposing portion or the mark.

According to one embodiment, the cover portion has a topped cylindrical shape having a top wall portion from which the substrate holding portion and the battery holding portion are suspended, and the substrate holding portion and the battery holding portion are disposed in positions which deviate in opposite directions to each other with respect to a center axis of the cover portion.

According to this configuration, even though the cover portion is attempted to be attached to the base portion with its orientation reversed 180° with respect to the center axis, for example, the substrate holding portion and the battery holding portion are in the positional relationship in which they deviate in the opposite directions to each other; therefore, the cover portion can be prevented from being attached to the base portion with its orientation reversed 180°, whereby the first antenna can be disposed to oppose the opposing portion or the mark.

According to one embodiment, a sensor is mounted on the base portion, and a second antenna is provided on the substrate, the second antenna being configured to transmit a measurement result of the sensor to the outside of the cover portion.

According to this configuration, the radio equipment can execute provisioning via the first antenna to join a radio network and then execute far distance communication in which, for example, the radio equipment transmits the measurement result of the sensor to the outside of the cover portion via the second antenna.

According to one embodiment, the first antenna is a loop antenna, and the second antenna is a chip antenna disposed inside the loop antenna.

According to this configuration, the loop antenna, which is the first antenna, and the chip antenna, which is the second antenna, can be disposed in a limited space in a space conserved fashion.

According to the disclosure that has been described heretofore, the radio equipment can be provided which improves the sensitivity of the near field communication.

BRIEF DESCRIPTION OF THE DRAWINGS

In the accompanying drawings:

FIG. 10A is a schematic drawing describing an erroneous attachment preventing function provided to the cover portion of the radio equipment illustrated in FIG. 1 to prevent an erroneous attachment of the cover portion to the base portion; and FIG. 10B is a schematic drawing describing the erroneous attachment preventing function provided to the cover portion of the radio equipment illustrated in FIG. 1 to prevent an erroneous attachment of the cover portion to the base portion.

DETAILED DESCRIPTION

Hereinafter, an embodiment of the disclosure will be described by reference to the drawings.

Figure 1:
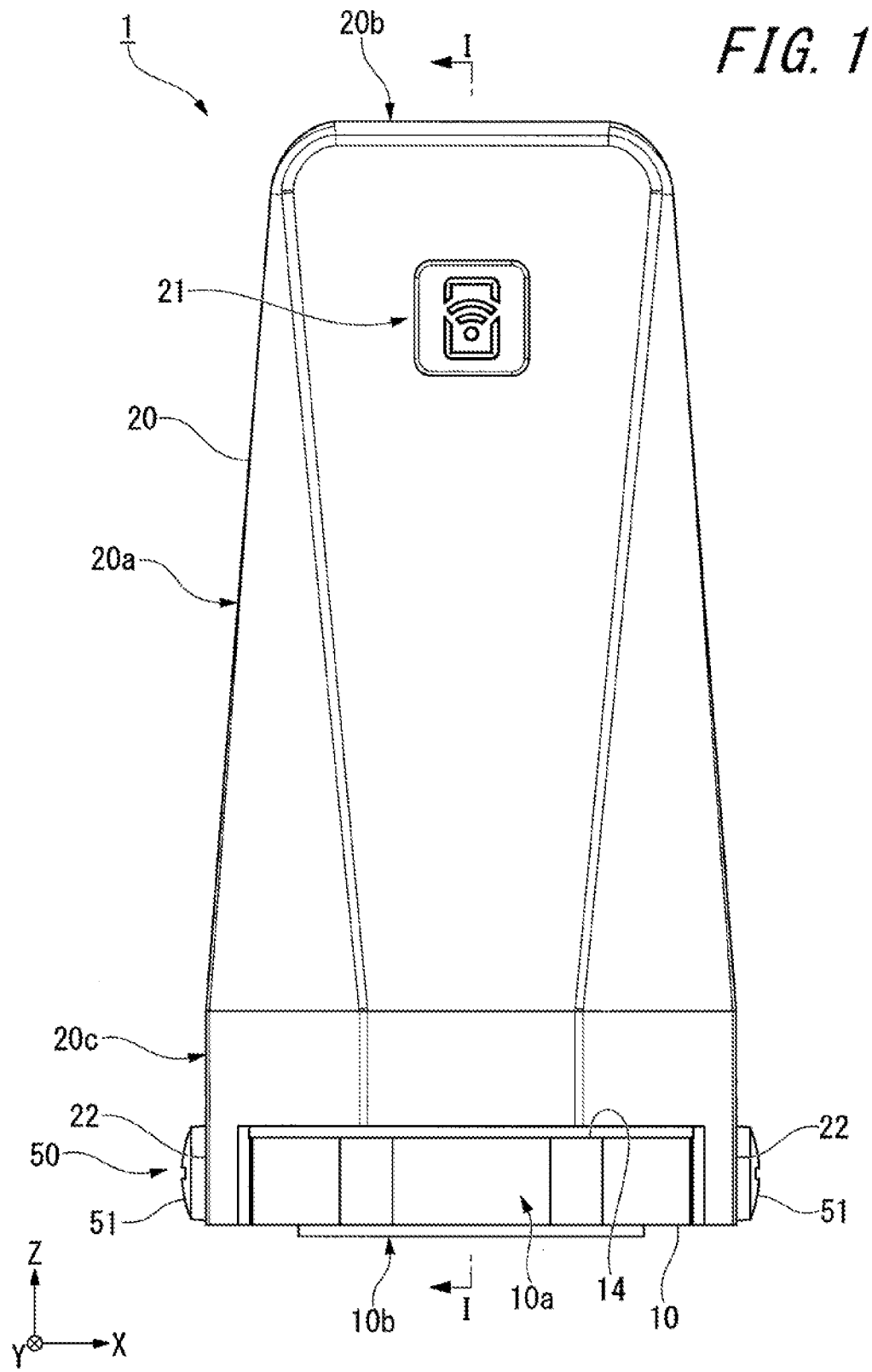
FIG. 1 is a front view of radio equipment of an embodiment of the disclosure.
Figure 2:
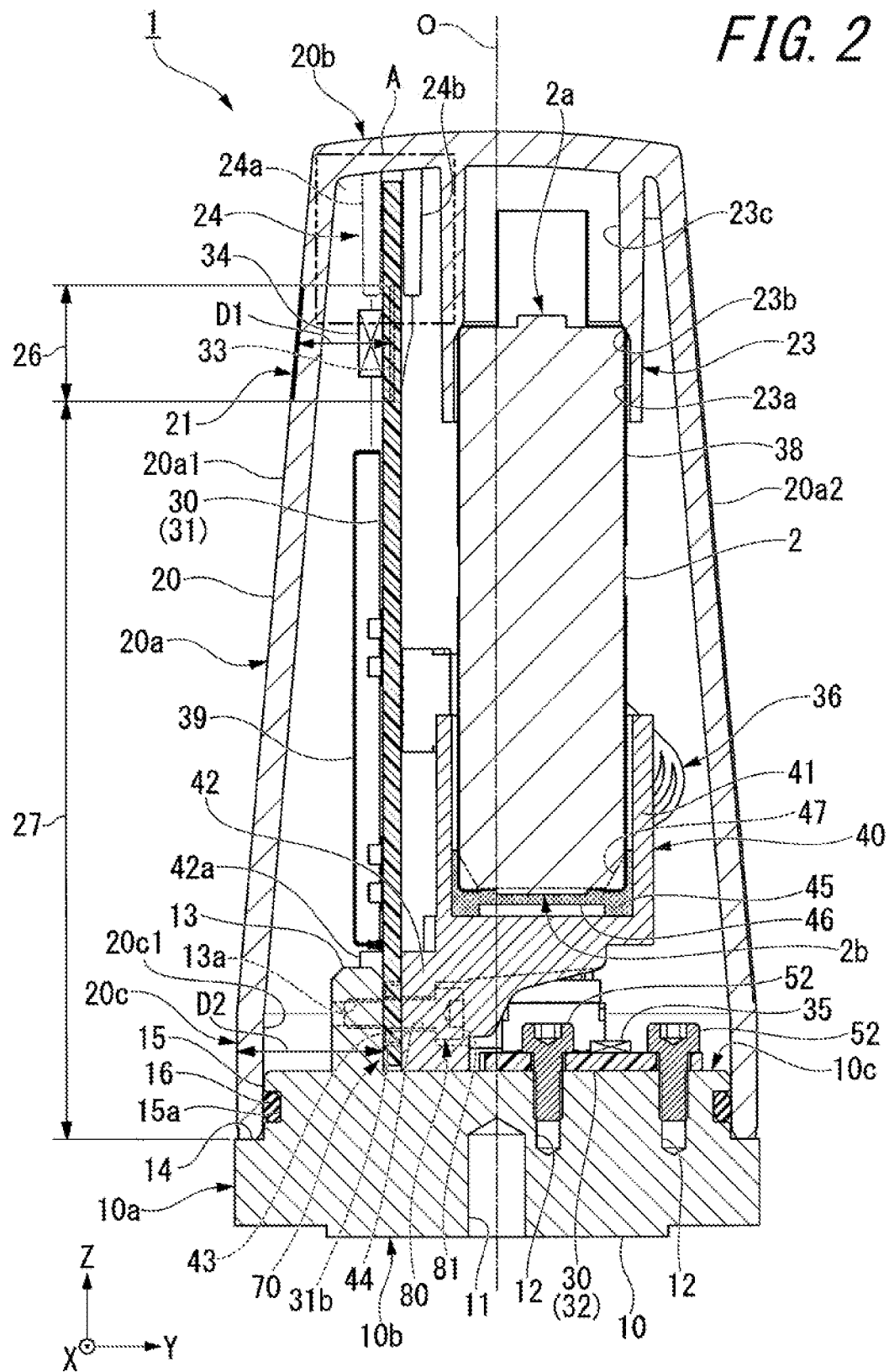
FIG. 2 is a sectional view of the radio equipment taken along a line I-I in FIG. 1.

Radio equipment 1 includes a base portion 10 and a cover portion 20 as illustrated in FIG. 1 and accommodates a substrate 30 inside the cover portion 20 as illustrated in FIG. 2, and a battery 2, a first antenna 33, a second antenna 34 and a sensor 35 are mounted on the substrate 30. In this embodiment, the radio equipment 1 is described as including the sensor 35 (a measuring apparatus). However, for example, when the radio equipment 1 constitutes a relay device or the like for the radio network and has only a communication function, the sensor 35 may not be provided.

Figure 5:
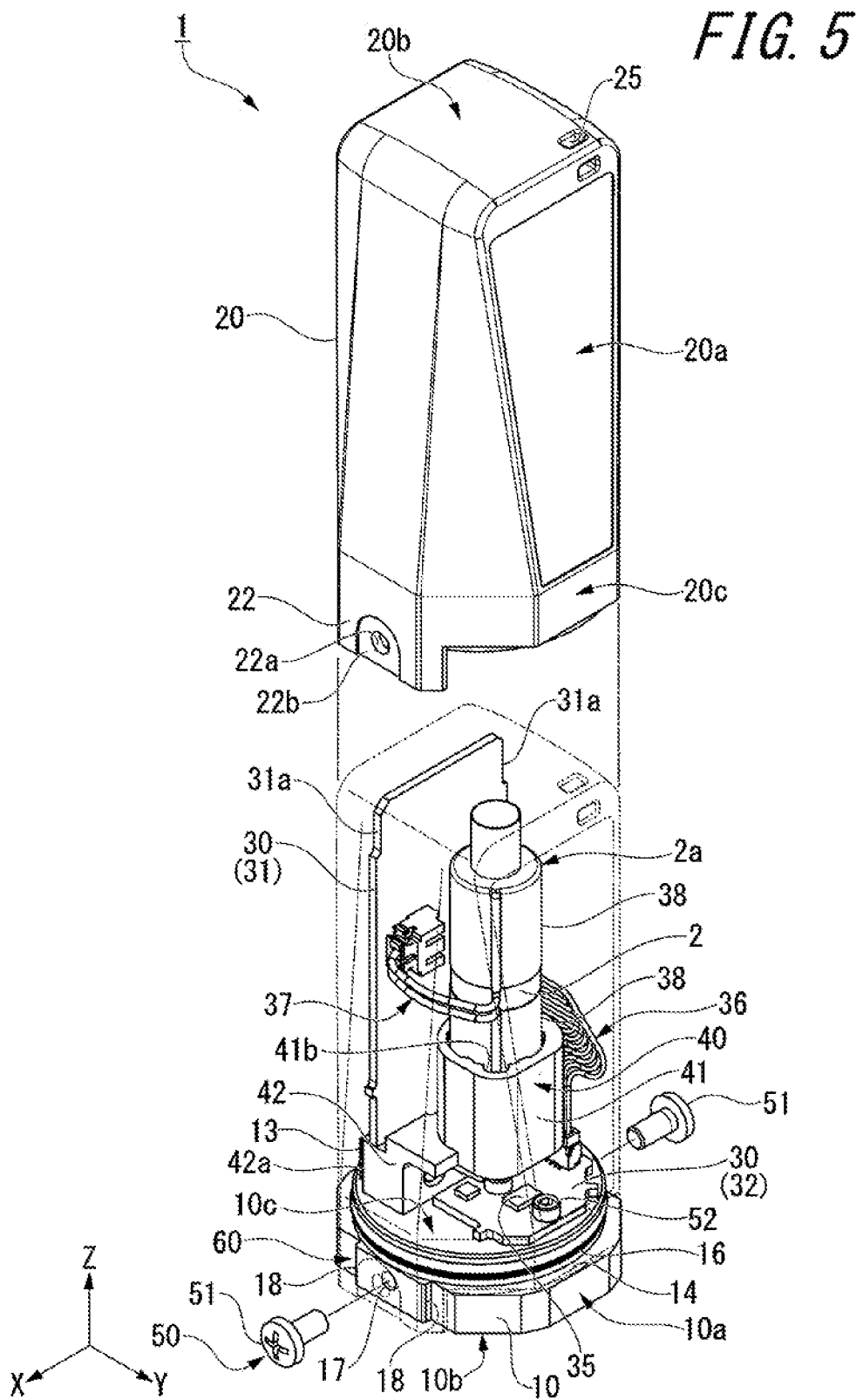
FIG. 5 is a rear exploded perspective view of the radio equipment illustrated in FIG. 1.

As illustrated in FIG. 5, the base portion 10 has a circular disc shape, and the cover portion 20 has a topped cylindrical shape. In the following description, an X-Y-Z orthogonal coordinate system is set, so that positional relationships among the constituent members are described while referring to this X-Y-Z orthogonal coordinate system from time to time. A center axis O (refer to FIG. 2) is shared commonly by the base portion 10 having the circular disc shape and the cover portion 20 having the topped cylindrical shape. Then, a direction in which the commonly shared center axis O extends will be referred to as a Z-axis direction, a direction which is at right angles to the Z-axis direction will be referred to as an X-axis direction, and a direction which is at right angles to both the Z-axis direction and the X-axis direction will be referred to as a Y-axis direction. The X-axis direction denotes a left-and-right direction of the radio equipment 1, the Y-axis direction denotes a front-and-rear direction of the radio equipment 1, and the Z-axis direction denotes a height direction of the radio equipment 1.

The base portion 10 constitutes a bottom portion of the radio equipment 1 as illustrated in FIG. 1. The base portion 10 is made up of a circular disc-shaped metallic material. An outer circumferential surface 10a of the base portion 10 has a polyhedral shape. A screw hole 11 is formed in a bottom surface 10b of the base portion 10 as illustrated in FIG. 2. The screw hole 11 is provided to screw the radio equipment 1 to an attachment target object, not illustrated (for example, an electric motor). The screw hole 11 is disposed concentrically with the center axis O, and the base portion 10 can be screwed up or down by gripping on the polyhedral outer circumferential surface 10a with a wrench.

Screw holes 12 are formed in a top surface 10c of the base portion 10 to fix the substrate 30 (a second substrate 32) to the base portion 10. The screw holes 12 are formed individually in two positions which evade the screw hole 11 as seen from above the base portion 10, whereby the second substrate 32 on which the sensor 35 is mounted can be screwed down to the base portion 10 in a replaceable fashion. The sensor 35 is intended to measure a physical parameter of the attachment target object, and in this embodiment, the sensor 35 is designed to measure vibrations of the attachment target object. In addition to the sensor configured to measure vibrations, the sensor 35 may be a sensor configured to measure various types of physical parameters such as temperature, humidity, pressure, speed, acceleration and revolution speed, for example.

A fixing portion 13 is formed on the top surface 10c of the base portion 10. This fixing portion 13 is configured to fix in place the first substrate 31, on which the first antenna 33 and the second antenna 34 are mounted, and a receiving portion 40, which will be described later. The fixing portion 13 constitutes a projecting wall portion which is erected perpendicularly with respect to the top surface 10c and is disposed in a position lying spaced away in the Y-axis direction (a −Y side) from the center axis O. The fixing portion 13 extends in the X-axis direction, and two screw holes 13a, which penetrate the fixing portion 13 in the Y-axis direction, are formed at two locations so as to be spaced apart from each other in the X-axis direction (refer to FIG. 8).

As illustrated in FIG. 2, a step portion 14, which is stepped down one level with respect to the top surface 10c, is formed on a circumferential edge portion of the base portion 10 which is situated on a top surface 10c side of the base portion 10. A bottom portion 20c of the cover portion 20 is seated on the step portion 14. Being different from the polyhedral outer circumferential surface 10a, a second outer circumferential surface 15 of the base portion 10 where the step portion 14 is formed is formed into a cylindrical curved surface. An annular groove 15a is formed on the second outer circumferential surface 15, and a seal ring 16 is disposed in this annular groove 15a.

The substrate 30 includes the first substrate 31 and the second substrate 32. The first substrate 31 is fixed to the fixing portion 13 and is erected perpendicularly with respect to the top surface 10c of the base portion 10. The second substrate 32 is disposed on the top surface 10c of the base portion 10 and is fixed to the top surface 10c with screws 52 which screw into the corresponding screw holes 12. The sensor 35 described above is mounted on the second substrate 32. The first antenna 33 for near distance communication and the second antenna 34 for far distance communication are mounted on the first substrate 31.

The first substrate 31 and the second substrate 32 are electrically connected together by way of a first connector cable 36 as illustrated in FIG. 5. The first substrate 31 is electrically connected to the battery 2 by way of a second connector cable 37. This enables electric power to be supplied from the battery 2 to the sensor 35. The second connector cable 37 is connected to a terminal, not illustrated, which connects to a top portion 2a (+) of the battery 2 and a terminal, not illustrated, which connects to a bottom portion 2b (−) of the battery 2 by way of two cables. The top portion 2a and the bottom portion 2b of the battery 2 are covered with a thermally shrinkable tube 38 configured to fix those terminals, not illustrated. Additionally, a shield 39 configured to protect other electronic equipment, not illustrated, such as a processor (refer to FIG. 2) and an insulation seal, not illustrated, are attached to the substrate 30.

Figure 3:
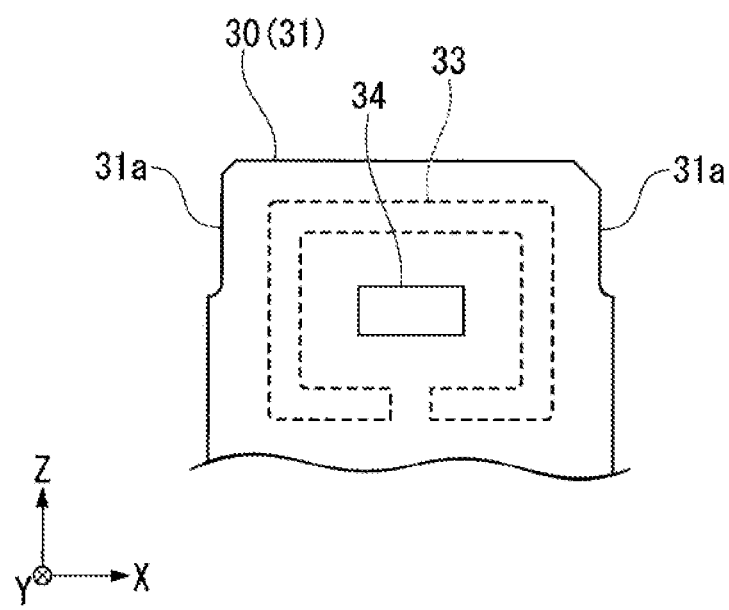
FIG. 3 is a front view of a first antenna and a second antenna mounted on a substrate provided on the radio equipment illustrated in FIG. 1.

As illustrated in FIG. 3, the first antenna 33 constitutes a loop antenna which is embedded in the first substrate 31, and the second antenna 34 constitutes a chip antenna which is disposed inside the loop antenna. The first antenna 33 may be formed on a surface of the first substrate 31. The second antenna 34 is designed to transmit a measurement result (sensor data) obtained by the sensor 35 to an outside of the cover portion 20. Thus, the second antenna 34 transmits sensor data to outside by way of a radio network, not illustrated, for example. The first antenna 33 is designed to execute provisioning through non-contact communication. The provisioning is a process of performing necessary settings to allow the radio equipment 1 to join the radio network.

The first antenna 33 executes transmission through near field communication (NFC). NFC means a communication (a non-contact communication) which can be executed when communication devices are spaced several tens centimeters or less apart from each other. The NFC includes a communication which is executed with casings of communication devices kept in contact with each other. In this NFC, one of two communication devices can be fed from the other in a non-contact fashion. The radio equipment 1, which can execute the NFC described above, can communicate with information terminal equipment such as a smartphone, a tablet-type personal computer and a note-type personal computer which are capable of performing NFC.

A mark 21 indicating the position of the first antenna 33 is formed on an outer surface of the cover portion 20 as illustrated in FIG. 1. The surface of a side wall portion 20a of the cover portion 20 where the mark 21 is provided is referred to as a front surface of the radio equipment 1. In this embodiment, the mark 21 is made up of a groove or is formed through stamping. However, the mark 21 may be made up of a seal or may be formed through marking. The radio equipment 1 can communicate with information terminal equipment through NFC by way of the first antenna 33 by moving the information terminal equipment described above towards the mark 21.

The cover portion 20 has an attachment piece 22 which projects downwards (towards a −Z side) from the bottom portion 20c. Specifically, a pair of left and right attachment pieces 22 is provided to face each other across the center axis O (at intervals of 180°). A through hole 22a and a countersunk portion 22b are formed in each of the pair of attachment pieces 22 as illustrated in FIG. 5. The through hole 22a penetrates the attachment piece 22 in the X-axis direction, and the countersunk portions is formed around the through hole 22a. Screw holes 17 are formed in the outer circumferential surface 10a of the base portion 10, and these screw holes 17 face the corresponding through holes 22a with the cover portion 20 attached to the base portion 10.

A screw 51 can be inserted through each of the through hole 22a to screw into the corresponding screw hole 17. The cover portion 20 is screwed on to the outer circumferential surface 10a of the base portion 10 by tightening the screws 51. Thus, the radio equipment 1 includes a screwing mechanism 50 configured to screw the cover portion 20 to the outer circumferential surface 10a of the base portion 10. This screwing mechanism 50 includes the attachment pieces 22 described above, the through holes 22a formed in the attachment pieces 22, the screw holes 17 formed on the outer circumferential surface 10a of the base portion 10 and the screws 51 which are inserted through the through holes 22a to be screwed into the screw holes 17.

The radio equipment 1 includes a rotation restricting mechanism 60 configured to restrict a relative rotation (so-called loosening) occurring about the screws 51 between the base portion 10 and the cover portion 20 in the screwing mechanism 50. The rotation restricting mechanism 60 is formed by cutaways 18 formed on the outer circumferential surface 10a of the base portion 10 illustrated in FIG. 5 and engaging grooves 22c formed inside the attachment pieces 22 of the cover portion 20 illustrated in FIG. 6. The cutaways 18 are formed in pair on both sides of each of the screw holes 17 so as to provide a step in the X-axis direction and extend in parallel in the Z-axis direction, as illustrated in FIG. 5. The pair of cutaways 18 forms X-Z planes on both sides of each of portions on the outer circumferential surface 10a of the base portion 10 where the screw hole 17 is formed and make this screw hole 17 forming a projecting portion.

The engaging groove 22c is formed into a recess having a pair of side surfaces (X-Z planes) which can face the pair of cutaways 18 (X-Z planes) so as to accommodate the portion of the base portion 10 where the screw hole 17 is formed (the projecting portion). The pair of side surfaces of the engaging grooves 22c are brought into abutment with the pair of cutaways 18, whereby a relative rotation occurring about the screws 51 (the X axis) between the base portion 10 and the cover portion 20 can be restricted. The pair of side surfaces of the engaging grooves 22c slide on the pair of cutaways 18 in the Z-axis direction, whereby the rotation restricting mechanism 60 can guide the base portion 10 and the cover portion 20 for attachment to or detachment from each other.

The cover portion 20 is made up of a topped cylindrical resin-molded material and includes the side wall portion 20a. As illustrated in FIG. 1, in the side wall portion 20a, an external shape of a top wall portion 20b is smaller than an external shape of the bottom portion 20c. Thus, the side wall portion 20a has an external shape which is reduced gradually from the bottom portion 20c towards the top wall portion 20b. When referred to herein, the external shape means an outer contour of the cover portion 20 in a section (the X-Z plane) which intersects the center axis O (the Z axis) at right angles. Additionally, that the external shape is smaller at the top wall portion 20b than at the bottom portion 20c means a state where an outer contour of the top wall portion 20b stays in an inner area of an outer contour of the bottom portion 20c when the cover portion 20 is seen from above along the center axis O.

Figure 6:
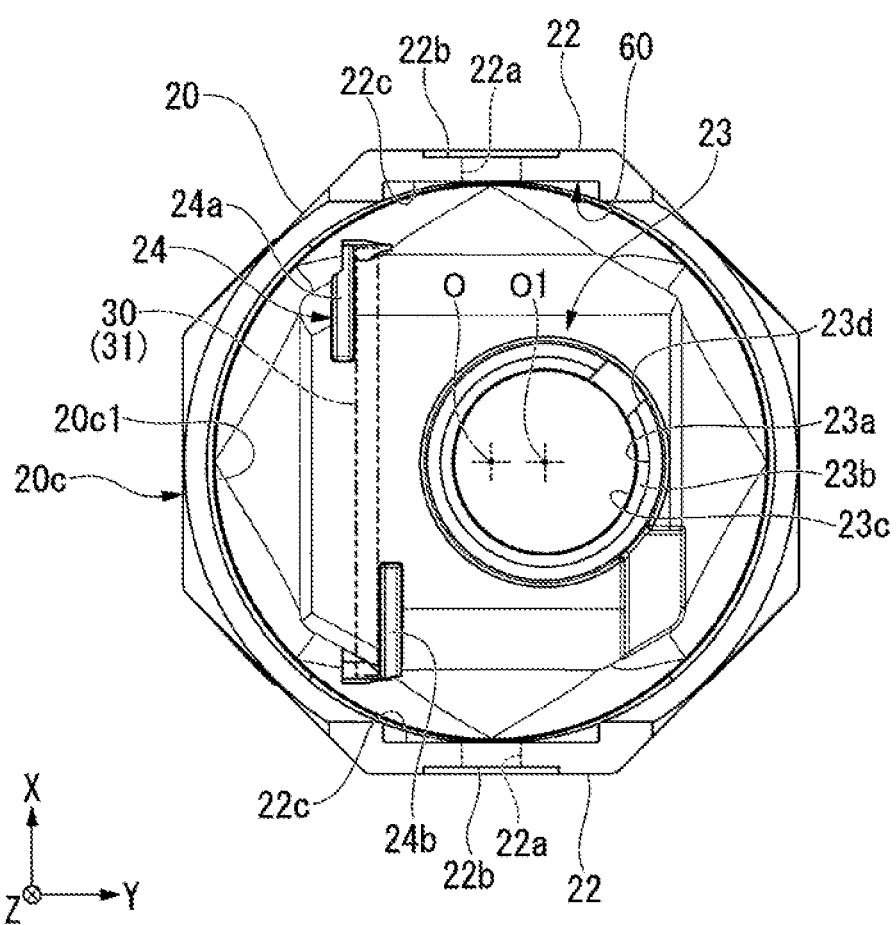
FIG. 6 is a bottom view of a cover portion provided on the radio equipment illustrated in FIG. 1.
Figure 7:
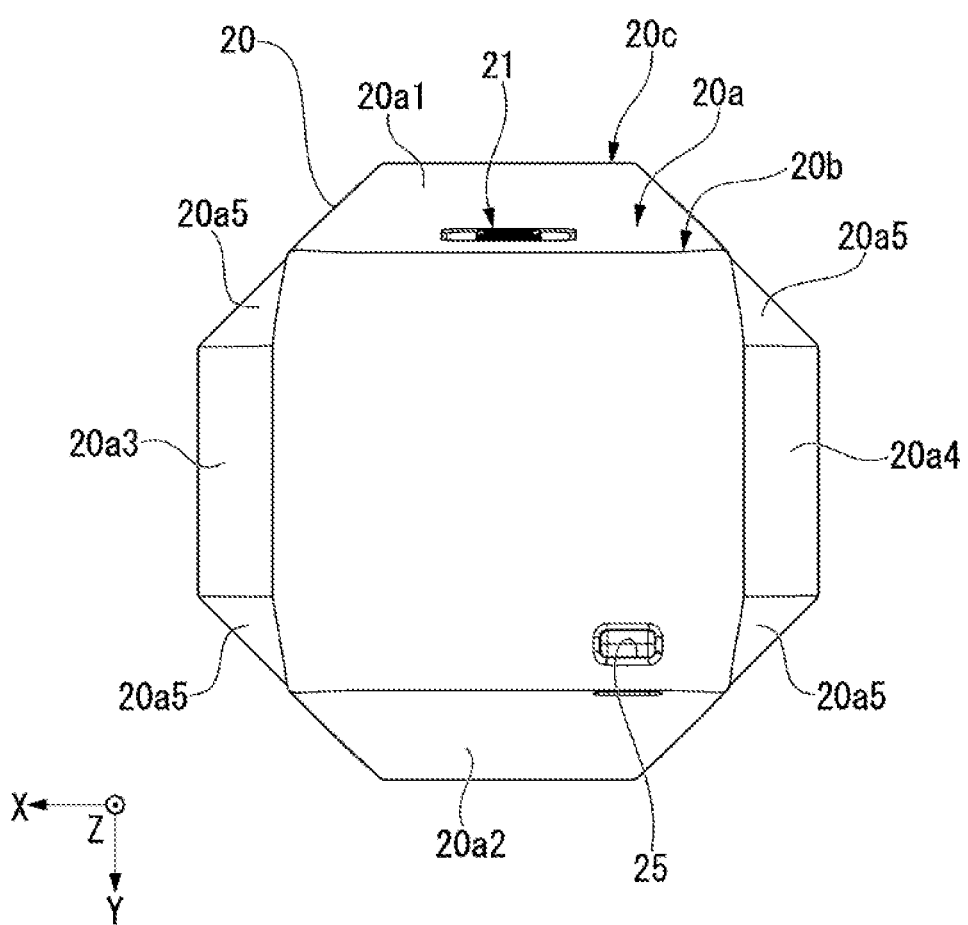
FIG. 7 is a plan view of the cover portion provided on the radio equipment illustrated in FIG. 1.

Specifically, as illustrated in FIG. 7, the bottom portion 20c has a substantially octagonal external shape. The top wall portion 20b has a substantially quadrangular external shape. In the side wall portion 20a, the front surface 20a1 where the mark 21 is formed and an opposite rear surface 20a2 have a substantially trapezoidal shape in which a bottom side is shorter than a top side. A left side surface 20a3 and a right side surface 20a4 of the side wall portion 20a have a substantially rectangular shape. Four connecting surfaces 20a5 which connect sloping sides of the substantially trapezoidal shapes of the front surface 20a1 and the rear surface 20a2 and long sides of the substantially rectangular shapes of the left side surface 20a3 and the right side surface 20a4, which are adjacent to this sloping side, together each have a substantially triangular shape. However, as illustrated in FIG. 6, an inner surface 20c1 of the bottom portion 20c constitutes an inner circumferential surface having a constant diameter, which differs from a polyhedral inner surface of the side wall portion 20a described above. This enables a gap between the base portion 10 and the cover portion 20 to be sealed up fluid-tightly by means of the seal ring 16, as illustrated in FIG. 2.

The external shape of the cover portion 20 is not limited to that shape. When the bottom portion 20c has the substantially octagonal external shape as in this embodiment, the top wall portion 20b may have, for example, a triangular or polygonal external shape of a pentagon or greater, a circular external shape, an elliptic external shape, a barrel-like external shape, a rhombus external shape or other heteromorphic external shapes (a shape formed only by curved surfaces such as a waveform and the like, or a shape resulting from cutting away part of the polygonal shapes or the circular shape described above rectilinearly (in plane)). The bottom portion 20c may have a polygonal external shape of triangle to heptagon, a polygonal external shape of enneagon or greater, a circular external shape, an elliptic external shape, a barrel-like external shape, a rhombus external shape or other heteromorphic external shapes. The external shape of the bottom portion 20c and the external shape of the top wall portion 20b may be similar but are different in size (similar shapes).

The external shape of the cover portion 20 is not limited to the shape which gradually reduces diametrically from the bottom portion 20c to the top wall portion 20b as in this embodiment. For example, the external shape of the cover portion 20 may reduce diametrically step by step. For example, the cover portion 20 may have an external shape in which stair-steps are formed on the outer surface of the cover portion 20 so that the external shape reduces diametrically step by step from the bottom portion 20c to the top wall portion 20b. Only one stair-step may be formed on the outer surface of the cover portion 20. For example, the cover portion 20 may have an external shape in which an external shape of an upper side of the cover portion 20 including an opposing portion 26 illustrated in FIG. 2, which will be described below, is smaller than an external shape of the cover portion 20 which is situated below the opposing portion 26 (hereinafter, referred to as a non-opposing portion 27).

As illustrated in FIG. 2, the cover portion 20 includes the opposing portion 26 configured to oppose the first antenna 33 and the non-opposing portion 27 disposed closer to the base portion 10 than the opposing portion 26 in a direction in which the first substrate 31 is erected (the Z-axis direction). Here, the opposing portion 26 means a range on the outer surface of the cover portion 20 where the first antenna 33 is mounted in the erecting direction of the first substrate 31 (the Z-axis direction). To be more specific, the opposing portion 26 means a mounting range (an X-Z plane) of the first antenna 33 on the surface (the front surface 20a1 on which the mark 21 is formed) of the outer surface of the cover portion 20 which provides a shortest distance to the first substrate 31 on which the first antenna 33 is mounted in the Y-axis direction and does not include the rear surface 20a2.

The non-opposing portion 27 means a portion of the outer surface of the cover portion 20 which is situated closer to the base portion 10 (a −Z side) than the opposing portion 26 and includes part of the side wall portion 20a and the bottom portion 20c. To be more specific, when the non-opposing portion 27 is referred to in relation to the opposing portion 26, the non-opposing portion 27 means a portion on the surface (the front surface 20a1) of the outer surface of the cover portion 20 which provides the shortest distance to the first substrate 31 on which the first antenna 33 is mounted in the Y-axis direction, and this portion is situated closer to the base portion 10 than the opposing portion 26. A distance D1 from the outer surface of the cover portion 20 at the opposing portion 26 to the first substrate 31 (in the example illustrated in FIG. 2, a distance to a central position of the first antenna 33 in the Z-axis direction) is made shorter than a distance D2 from the outer surface of the cover portion at the non-opposing portion 27 to the first substrate 31 (in the example illustrated in FIG. 2, a distance from the bottom portion 20c where the external shape of the cover portion 20 is constant). D1 is smaller, for example, by on the order of 20 to 40% than D2.

As illustrated in FIG. 2, a battery holding portion 23 configured to hold the battery 2 and a substrate holding portion 24 configured to hold the substrate 30 are provided on the top wall portion 20b of the cover portion 20 so as to be suspended from the top wall portion 20b. The battery holding portion 23 has a cylindrical shape so as to be brought into engagement with the top portion 2a of the battery 2 with the cover portion 20 attached to the base portion 10. The substrate holding portion 24 holds the upper end portion of the first substrate 31 with the cover portion 20 attached to the base portion 10 and is formed into a pair of plates (a first plate portion 24a and a second plate portion 24b, which will both be described later) which face a front side and a rear side of the upper end portion, respectively. The battery holding portion 23 and the substrate holding portion 24 have different shapes and are disposed in positions (the +Y side and the −Y side) which deviate in opposing directions to each other with respect to the center axis O of the cover portion 20.

The battery holding portion 23 includes a first accommodating portion 23a configured to accommodate the top portion 2a of the battery 2, a diametrically contracted portion 23b provided contiguously with the first accommodating portion 23a, a second accommodating portion 23c provided contiguously with the diametrically contracted portion 23b and to accommodate the thermally shrinkable tube 38 extending upwards from the top portion 2a of the battery 2. In the diametrically contracted portion 23b, an inside diameter is gradually reduced in the direction in which the cover portion 20 is attached to or detached from the base portion 10 (the Z-axis direction) as the diametrically contracted portion 23b extends towards the top portion 2a (a +Z side) of the battery 2 with the cover portion 20 attached to the base portion 10. A cutaway 23d (refer to FIG. 6) is formed in the cylindrical battery holding portion 23 for passage of the second connector cable 37. As illustrated in FIG. 6, the center axis O1 of the battery holding portion 23 deviates towards the +Y side with respect to the center axis O of the cover portion 20. In this embodiment, the battery holding portion 23 has the cylindrical shape since the object is the battery 2 having the cylindrical shape. However, when the object has a shape (for example, a prism shape) other than the cylindrical shape, the battery holding portion 23 preferably has a cylindrical shape matching the shape of the object (for example, an angularly cylindrical shape).

The substrate holding portion 24 includes the first plate portion 24a facing the front side of the first substrate 31 and the second plate portion 24b facing the rear side of the first substrate 31. The first plate portion 24a is formed so as to straddle a corner portion between an inner side surface on a +X side of the side wall portion 20a and a lower surface of the top wall portion 20b. The second plate portion 24b is formed so as to straddle a corner portion between an inner side surface on a −X side of the side wall portion 20a and a lower surface of the top wall portion 20b. The first plate portion 24a and the second plate portion 24b are not disposed so as to overlap each other in the front-and-rear direction (the Y-axis direction) but are disposed so as to be staggered or not in line with each other. This substrate holding portion 24 is disposed on the −Y side with respect to the center axis O of the cover portion 20.

Figure 9:
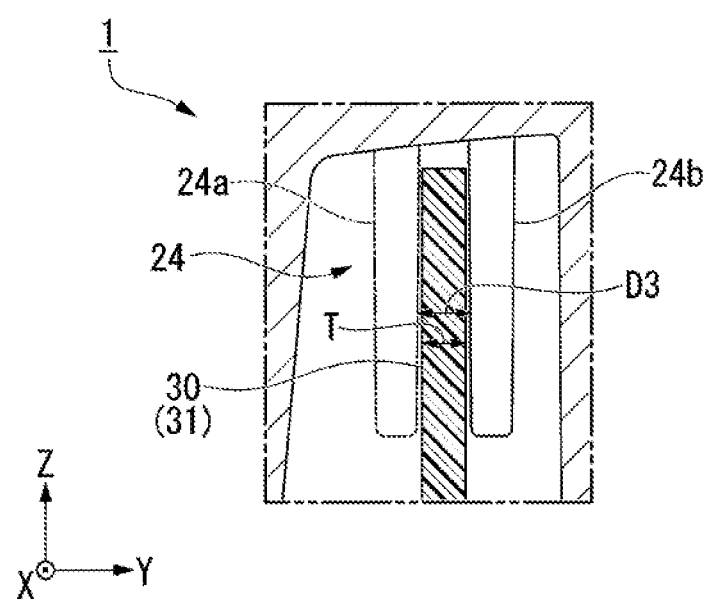
FIG. 9 is an enlarged view of an area A illustrated in FIG. 2.

As illustrated in FIG. 9, when assuming that a thickness of the first substrate 31 is T, D3, which denotes a gap defined between the first plate portion 24a and the second plate portion 24b, is made greater than T. For example, D3 is greater by on the order of 5 to 15% than T. D3, which denotes the gap defined between the first plate portion 24a and the second plate portion 24b, may be constant over an overall range in the erecting direction of the first substrate 31 (the Z-axis direction) or may gradually reduce (tapers) upwards in the first substrate erecting direction. A dimension of the first substrate 31 in a thickness direction (the Y-axis direction) varies, and hence, D3 is preferably set with a greater tolerance than T.

Figure 8:
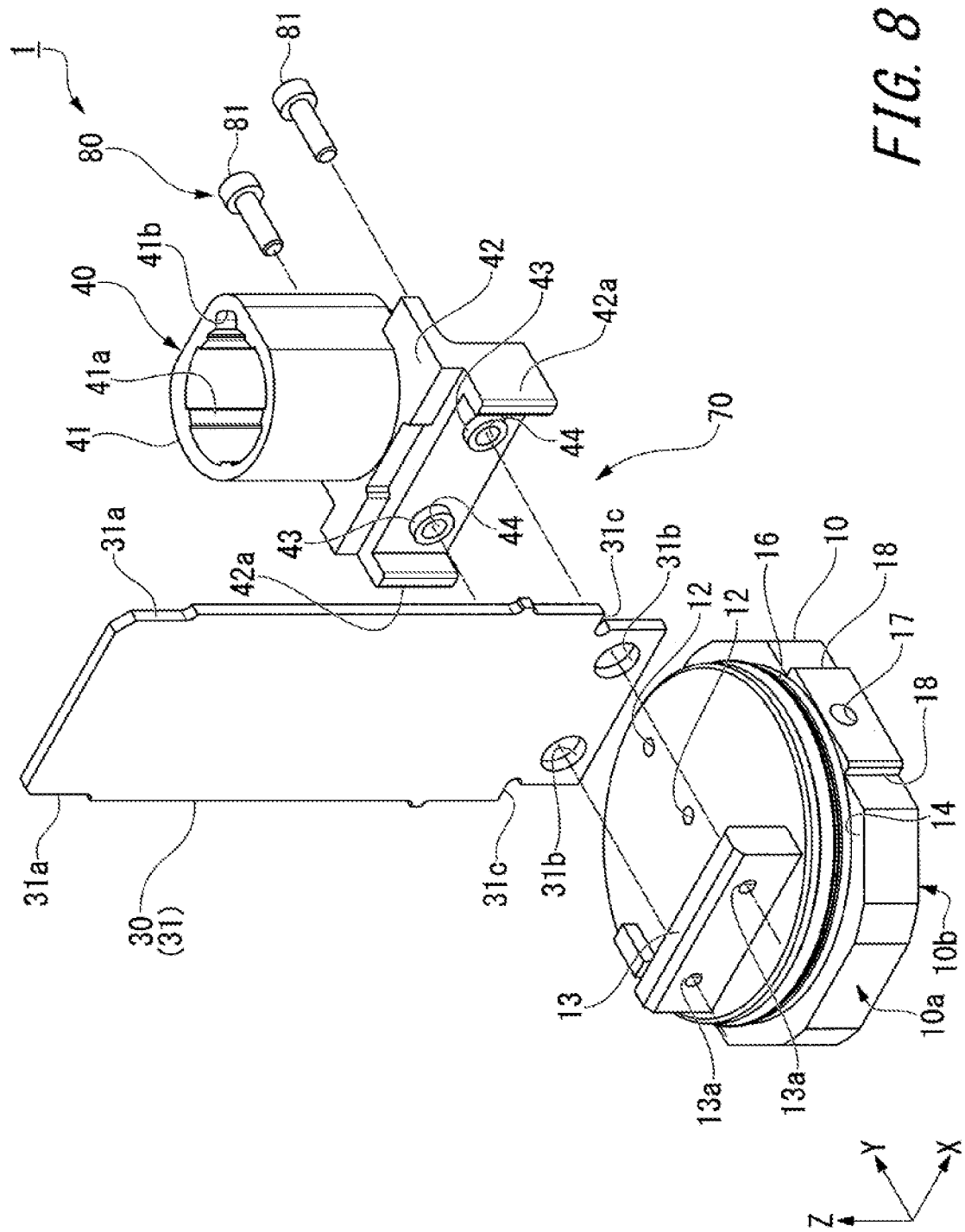
FIG. 8 is an exploded perspective view of a base portion, the substrate and a receiving portion which are provided on the radio equipment illustrated in FIG. 1.

Returning to FIG. 2, the base portion 10 has the receiving portion 40 configured to support the longitudinally bottom portion 2b of the battery 2. The receiving portion 40 includes a main body portion 41 having a bottomed cylindrical shape and configured to support the bottom portion 2b of the battery 2 and a support portion 42 provided contiguously with a bottom portion of the main body portion 41 and configured to support the main body portion 41 above the second substrate 32. As illustrated in FIG. 8, the support portion 42 includes boss portions 43 configured to be brought into engagement with the first substrate 31 and through holes 44 formed so as to penetrate the corresponding boss portions 43. The through holes 44 can face the corresponding screw holes 13a formed in the fixing portion 13 on the base portion 10. Then, the receiving portion 40 is attached to the base portion 10 together with the first substrate 31 by screwing screws 81 through the through holes 44 into the screw holes 13a.

Specifically, as illustrated in FIG. 8, the support portion 42 is formed into an inverted L shape, and the cylindrical boss portions 43 are provided on a front side (a −Y side) which faces the first substrate 31 so as to project therefrom.

Through holes 31b are formed in a lower portion of the first substrate 31 so that the cylindrical boss portions 43 can be inserted through them. The boss portions 43 and the through holes 31b are each formed in pair so as to match the screw holes 13a of the fixing portion 13. Ribs 41a are formed at intervals in a circumferential direction on an inner circumferential surface of the main body portion 41 supported on the support portion 42, and a groove 41b is formed on the inner circumferential surface for passage of the second connector cable 37.

The support portion 42 includes a pair of support ribs 42a configured to hold the first substrate 31 therebetween in a left-and-right width direction (the X-axis direction). A pair of cutaways 31c is formed at the lower portion of the first substrate 31 which can rest on upper surfaces of the pair of support ribs 42a. As illustrated in FIG. 2, with the pair of cutaways 31c resting on the upper surfaces of the pair of support ribs 42a, a lower end of the first substrate 31 is not in contact with the top surface 10c of the base portion 10. This is because a longitudinal dimension of the first substrate 31 varies. A length (a projecting amount) of the boss portions 43 is made smaller than a thickness of the first substrate 31. A pair of cutaways 31a formed in an upper portion of the first substrate 31 illustrated in FIG. 8 is designed to avoid an interference with the cover portion 20 whose external shape is smaller.

The boss portions 43 are inserted through the through holes 31b, and the pair of cutaways 31c rests on the upper surfaces of the pair of support ribs 42a, whereby the first substrate 31 can be brought into engagement with the receiving portion 40. In this way, the radio equipment 1 includes an engagement mechanism 70 configured to bring the first substrate 31 into engagement with the receiving portion 40. This engagement mechanism 70 includes the boss portions 43 formed on the support portion 42 described above, the pair of support ribs 42a, the through holes 31b formed in the first substrate 31 and the pair of cutaways 31c. The radio equipment 1 includes an attachment mechanism 80 configured to attach the first substrate 31 and the receiving portion 40, engaged with each other by the engagement mechanism 70, integrally to the base portion 10.

The attachment mechanism 80 includes the through holes 44 penetrating the boss portions 43, the screw holes 13a formed in the fixing portion 13 of the base portion 10, and the screws 81 passed through the through holes 44 to be screwed into the screw holes 13a. A length (a projecting amount) of the pair of support ribs 42a is made greater than the thickness of the first substrate 31, so that the pair of support ribs 42a can hold the fixing portion 13 of the base portion 10 therebetween in the left-and-right width direction (the X-axis direction) together with the first substrate 31. This can enable the receiving portion 40 with which the first substrate 31 is in engagement to be positioned properly with respect to the fixing portion 13, facilitating the screwing operation using the screws 81.

Returning to FIG. 2, an elastic portion 45 is provided on a bottom surface of the main body portion 41 of the receiving portion 40. The elastic portion 45 is formed of an elastic material such as a silicone rubber, for example. The elastic portion 45 is brought into abutment with the bottom portion 2b of the battery 2 and can be deformed elastically in the direction in which the cover portion 20 is attached to or detached from the base portion 10 (the Z-axis direction). Specifically, on a circumferential portion of a bottom surface of the elastic portion 45, a portion other than a circumferential portion (for example, a portion lying near a center) of the bottom surface is formed in a concave shape in upward direction, whereby a space is formed between the bottom surface of the main body portion 41 and the elastic portion 45. A relief groove 46 is formed on the bottom surface of the elastic portion 45 to form the space for elastic deformation of the elastic portion 45. In this embodiment, the relief groove 46 is formed on the bottom surface of the elastic portion 45 as the upwardly oriented concavity, but the relief groove 46 may be formed into downwardly oriented concavity on the bottom surface of the main body portion 41. A diametrically contracted elastic portion 47 is formed on an upper surface of the elastic portion 45. This diametrically contracted elastic portion 47 has an inside diameter which is reduced gradually as it extends towards the bottom surface (the −Z side) of the main body portion 41 in its restored state in which for example, the cover portion 20 is detached from the base portion 10, so that the battery 2 is removed from the main body portion 41 and the diametrically contracted elastic portion 47 is not in abutment with the bottom portion 2b of the battery 2 (a state indicated by a chain double-dashed line in FIG. 2). The diametrically contracted elastic portion 47 is elastically deformed by a corner portion at the bottom portion 2b of the battery 2. However, the diametrically contracted elastic portion 47 constitutes a tapered surface when it is in a restored state (a state where the battery 2 is removed from the main body portion 41).

Figure 4:
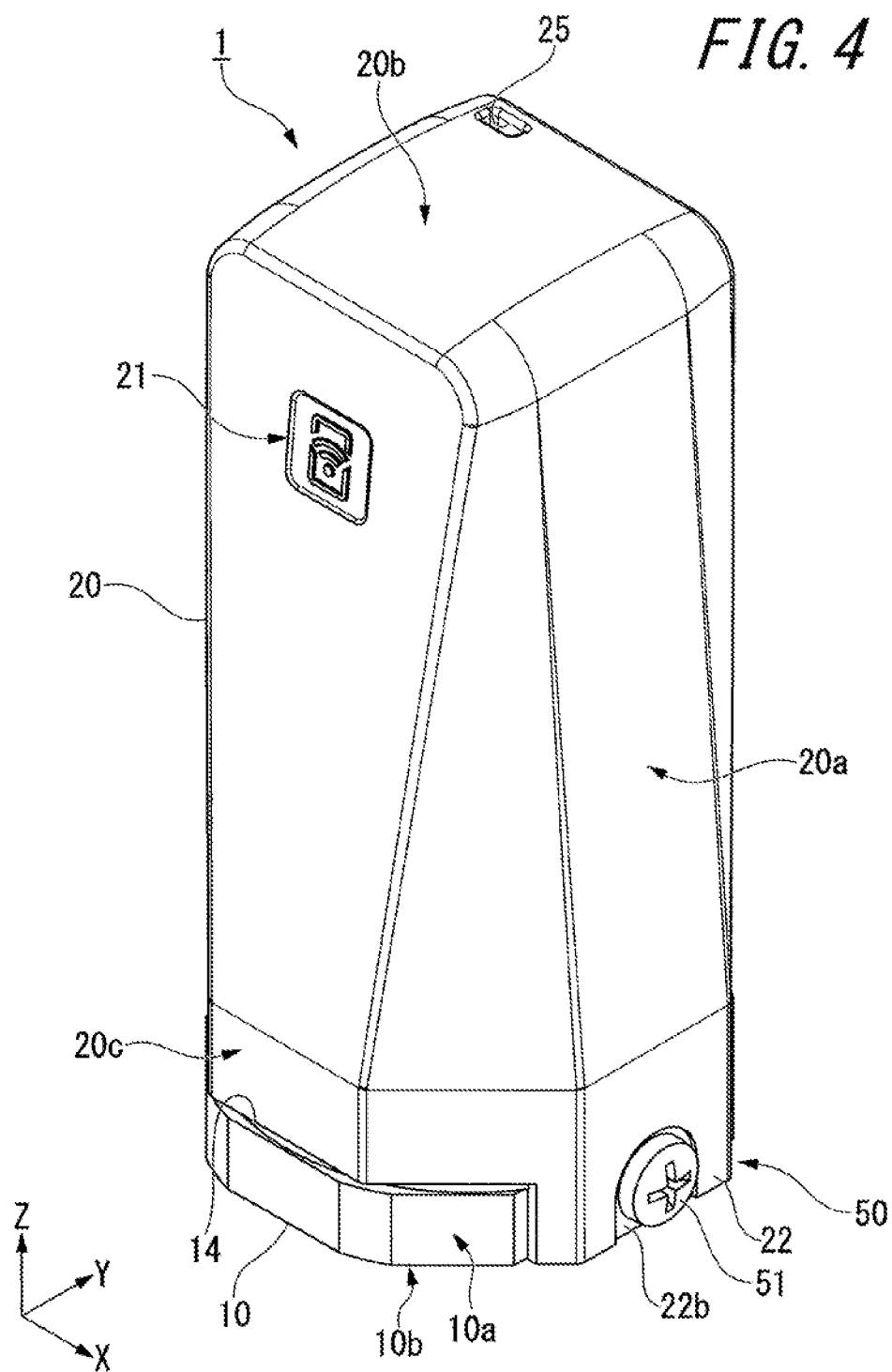
FIG. 4 is a front perspective view of the radio equipment illustrated in FIG. 1.

A string attachment hole 25 is formed in the top wall portion 20b of the cover portion 20 as illustrated in FIG. 4. The string attachment hole 25 is formed into an L shape extending from the top wall portion 20b to a rear side of the side wall portion 20a as illustrated in FIG. 5. A string-shaped member (a strap, for example), not illustrated, is passed through the string attachment hole 25, whereby the radio equipment 1 can be kept fastened to the attachment target object. For example, when the radio equipment 1 is magnetically secured to the attachment target object by means of a magnet or the like, there may be a risk of the radio equipment 1 falling off the attachment target object due to vibration or the like. However, with this configuration, the radio equipment 1 can be prevented from being lost or damaged.

Thus, as has been described heretofore, with the radio equipment 1 configured as described above, as illustrated in FIG. 2, the distance D1 from the outer surface of the cover portion 20 at the opposing portion 26 which opposes the first antenna 33 to the first substrate 31 is made shorter than the distance D2 from the outer surface of the cover portion 20 at the non-opposing portion 27 which does not oppose the first antenna 33 to the first substrate 31. Therefore, when compared with a case where a cylindrical cover portion is adopted in which the distance to the first antenna 33 varies little, the sensitivity of the near field communication is improved remarkably.

In this embodiment, the external shape of the cover portion 20 at the opposing portion 26 is smaller than the external shape of the cover portion 20 at the non-opposing portion 27, and therefore, even in the event that the mark 21 is not provided, the distance to the first substrate 31 is shorter or the front surface 20a1 of the cover portion 20 lies nearer to the first substrate 31 at the opposing portion 26 (the upper portion of the side wall portion 20a) than at the non-opposing portion 27 (for example, the bottom portion 20c) in every direction on the X-Y plane. Thus, when compared with a case where a cylindrical cover portion is adopted in which the distance to the first substrate 31 varies little, the sensitivity of the near field communication is improved.

Further, in this embodiment, the outer surface (the front surface 20a1) of the cover portion 20 where the opposing portion 26 is formed is formed into the flat plane. According to this configuration, since the front surface 20a1 of the cover portion 20 where the opposing portion 26 is formed constitutes the flat plane as with the first substrate 31, the space (the distance D1) defined between the front surface 20a1 and the first substrate 31 can be made smaller than a case where the cylindrical cover portion (the cover portion whose outer surface is made up of a curved surface), whereby the sensitivity of the near field communication can be improved further.

In this embodiment, the mark 21 (refer to FIG. 1) indicating the position of the first antenna 33 is formed at the opposing portion 26. According to this configuration, the position of the first antenna 33 can be determined from the outside of the cover portion 20, and therefore, the information terminal device can easily be moved towards the first antenna 33.

Further, in the embodiment, as illustrated in FIG. 2, the cover portion 20 includes the substrate holding portion 24 configured to dispose the first antenna 33 to oppose the mark 21. According to this configuration, the first antenna 33 can be positioned behind the mark 21 inside the cover portion 20. Thus, not only the position of the first antenna 33 can be determined from the outside of the cover portion 20, but also the sensitivity of the near field communication can be improved further.

In a case where the substrate holding portion 24 is provided on the cover portion 20 as described above, the cover portion 20 cannot be attached to the base portion 10 through screwing (rotation about the center axis O) as done conventionally. Thus, in this embodiment, as illustrated in FIG. 5, the radio equipment 1 includes the screwing mechanism 50 configured to screw the cover portion 20 down on to the outer circumferential surface 10a of the base portion 10. In this way, the cover portion 20 including the substrate holding portion 24 can be attached to the base portion 10 by screwing the cover portion 20 down on to the outer circumferential surface 10a of the base portion 10.

In a case where the screwing mechanism 50 is adopted as described above, the relative rotation (so-called loosening) between the base portion 10 and the cover portion 20 about the screws 51 (the X axis) tends to be generated easily due to the screwing mechanism 50. To cope with this, in this embodiment, the radio equipment 1 includes the rotation restricting mechanism 60 configured to restrict the relative rotation that would otherwise be generated between the base portion 10 and the cover portion 20 about the screws 51 due to the screwing mechanism 50. In this way, the adoption of the rotation restricting mechanism 60 can not only prevent the loosening between the cover portion 20 and the base portion 10 about the screws 51 but also suppress the deviation in the opposing positional relationship between the opposing portion 26 and the first antenna 33.

Further, in the embodiment, the rotation restricting mechanism 60 guides the base portion 10 and the cover portion 20 for attachment to or detachment from each other in a direction in which the first substrate 31 is erected. Specifically, the cover portion 20 is guided in the Z-axis direction as a result of the forming portion (the projecting portion) of the screw hole 17 on the base portion 10 formed by the cutaways 18 being brought into engagement with the engaging groove 22c formed into the recess. Thus, the attachment of the cover portion 20 to the base portion 10 is facilitated.

In this embodiment, as illustrated in FIGS. 2 and 6, the cover portion 20 includes the battery holding portion 23 configured to hold the battery 2 electrically connected with the first substrate 31. Then, the substrate holding portion 24 and the battery holding portion 23 have the different shapes. Thus, since the substrate holding portion 24 and the battery holding portion 23 have the different shapes, the battery holding portion 23 is never mounted on the first substrate 31. On the contrary, the substrate holding portion 24 is never mounted on the battery 2. Consequently, the cover portion 20 can be prevented from being attached reversely, whereby the first antenna 33 can be disposed to oppose the opposing portion 26 (the mark 21).

Further, the substrate holding portion 24 and the battery holding portion 23 are disposed in the positions which deviate in the opposite directions to each other with respect to the center axis O of the cover portion 20. Due to this, for example, as illustrated in FIG. 10A, when the cover portion 20 is attached to the base portion 10 in a proper orientation, the substrate holding portion 24 can be brought into engagement with the upper end portion of the first substrate 31, while the battery holding portion 23 can be brought into engagement with the top portion 2a of the battery 2. On the other hand, when the orientation of the cover portion 20 is reversed by 180° with respect to the center axis O as illustrated in FIG. 10B, the positional relationship between the substrate holding portion 24 and the battery holding portion 23 is reversed when compared with that illustrated in FIG. 10A. Then, for example, a lower end of the battery holding portion 23 comes into contact with an upper end of the first substrate 31, whereby the attachment of the cover portion 20 to the base portion 10 is interrupted. In this way, even when attempting to attach the cover portion 20 to the base portion with the orientation of the cover portion 20 reversed 180° with the center axis O, since the substrate holding portion 24 and the battery holding portion 23 are in the positional relationship in which they deviate from each other in the opposite directions, the cover portion 20 can be prevented from being attached to the base portion 10 with the cover portion 20 reversed 180°, whereby the first antenna 33 can oppose the opposing portion 26 (the mark 21).

In this embodiment, as illustrated in FIG. 2, a sensor 35 is mounted on the base portion 10, and a second antenna 34 is provided on the first substrate 31. This second antenna 34 is configured to transmit a measurement result of the sensor 35 to the outside of the cover portion 20. According to this configuration, the radio equipment 1 can execute the provisioning via the first antenna 33 to join the radio network and then execute far distance communication in which, for example, the radio equipment 1 transmits the measurement result of the sensor 35 to the outside of the cover portion 20 via the second antenna 34.

Further, in this embodiment, as illustrated in FIG. 3, the first antenna 33 is a loop antenna, and the second antenna 34 is a chip antenna disposed inside the loop antenna. According to this configuration, the loop antenna, which is the first antenna 33, and the chip antenna, which is the second antenna 34, can be disposed in a limited space in a space conserved fashion.

In this way, according to the embodiment of the disclosure, the radio equipment 1 includes the first substrate 31 on which the first antenna 33 for the near field communication is provided, the base portion 10 on which the first substrate 31 is erected, and the cover portion 20 attached to the base portion 10. The cover portion 20 includes the opposing portion 26 configured to oppose the first antenna 33 and the non-opposing portion 27 which is disposed closer to the base portion 10 than the opposing portion 26 in the erecting direction of the first substrate 31. The distance D1 from the outer surface of the cover portion 20 to the first substrate 31 at the opposing portion 26 is shorter than the distance D2 from the outer surface of the cover portion 20 to the first substrate 31 at the non-opposing portion 27. Thus, adopting this configuration can provide the radio equipment 1 having the good sensitivity for the near field communication.

Thus, while the preferred embodiment of this disclosure has been described by reference to the drawings, the disclosure is not limited to the embodiment described heretofore. The shapes and combinations of the constituent members illustrated in the embodiment are only the examples and hence can be modified variously based on design requirements without departing from the spirit and scope of the disclosure.

In the embodiment, the sensor 35 is described as being accommodated inside the cover portion 20. However, the disclosure is not limited to this configuration. For example, a configuration may be adopted in which the sensor is externally attached to the radio equipment 1 by way of a cable, so that measuring results are input into the radio equipment 1 from the sensor externally attached to the radio equipment 1. Specifically speaking, a configuration may be adopted in which a sensor for measuring a temperature is attached to a measurement target object, and a cable from the sensor is connected to the radio equipment 1, so that an output (for example, an analog voltage) is input into the radio equipment 1.

The battery 2 accommodated inside the cover portion 20 may supply electric power not only to the radio equipment 1 but also to an externally attached sensor as one described above.

In the embodiment, while the base portion 10 and the receiving portion 40 are configured as the separate members, the base portion 10 and the receiving portion 40 may be integrated into one member.

In the embodiment, while the mark 21 is described as being formed to indicate the position of the first antenna 33, the disclosure is not limited to this configuration. For example, the mark 21 may not be formed. For example, a part of the cover portion 20 is formed into a planar shape without being formed the mark 21, while the other portion is formed into a curved surface, and the substrate holding portion 24 is provided so that the first antenna 33 is disposed to face the flat surface portion (an opposing portion 26). According to this configuration, the position of the first antenna 33 can roughly be determined from the outside of the cover portion 20.

The invention claimed is:

1. Radio equipment comprising:
    a substrate on which a first antenna for near field communication is provided;
    a base portion on which the substrate is erected; and
    a cover portion configured to be attached to the base portion so as to cover the substrate,
    wherein the cover portion comprises an opposing portion configured to oppose the first antenna and a non-opposing portion disposed closer to the base portion than the opposing portion in a direction in which the substrate is erected, and
    wherein a distance from an outer surface of the cover portion to the substrate at the opposing portion is shorter than a distance from the outer surface of the cover portion to the substrate at the non-opposing portion,
    wherein a mark is formed on the opposing portion, the mark indicating a position where the first antenna is disposed; and
    wherein the cover portion comprises a substrate holding portion configured to dispose the first antenna to oppose the mark.

2. The radio equipment according to claim 1,
    wherein an external shape of the cover portion at the opposing portion is smaller than an external shape of the cover portion at the non-opposing portion.

3. The radio equipment according to claim 1,
    wherein the outer surface of the cover portion forming the opposing portion is formed into a flat plane.

4. The radio equipment according to claim 1,
    wherein the base portion has a circular disc shape and comprises a screwing mechanism configured to screw the cover portion to an outer circumferential surface of the base portion.

5. The radio equipment according to claim 4, comprising a rotation restricting mechanism configured to restrict a relative rotation occurring between the base portion and the cover portion about a screw due to the screwing mechanism.

6. The radio equipment according to claim 5,
    wherein the rotation restricting mechanism guides the base portion and the cover portion for attachment to or detachment from each other in a direction in which the substrate is erected.

7. The radio equipment according to claim 1,
    wherein the cover portion comprises a battery holding portion configured to hold a battery which is electrically connected with the substrate, and
    wherein the substrate holding portion and the battery holding portion have different shapes.

8. The radio equipment according to claim 7,
    wherein the cover portion has a topped cylindrical shape having a top wall portion from which the substrate holding portion and the battery holding portion are suspended, and
    wherein the substrate holding portion and the battery holding portion are disposed in positions which deviate in opposite directions to each other with respect to a center axis of the cover portion.

9. The radio equipment according to claim 1,
    wherein a sensor is mounted on the base portion, and
    wherein a second antenna is provided on the substrate, the second antenna being configured to transmit a measurement result of the sensor to the outside of the cover portion.

10. The radio equipment according to claim 9,
    wherein the first antenna is a loop antenna, and
    wherein the second antenna is a chip antenna disposed inside the loop antenna.

* * * * *